United States Patent [19]
Dixon et al.

[11] 3,988,430
[45] Oct. 26, 1976

[54] IMMUNOASSAY OF ANTIPYRINE

[75] Inventors: William Ross Dixon, Dumont; Alexander Wood, Hohokus, both of N.J.

[73] Assignee: Hoffmann-La Roche Inc., Nutley, N.J.

[22] Filed: Feb. 10, 1975

[21] Appl. No.: 548,656

[52] U.S. Cl. .............................. 424/1.5; 260/112 R; 424/88
[51] Int. Cl.$^2$ .................. G01N 33/00; A61K 39/00
[58] Field of Search .................. 424/1, 1.5, 12, 88, 424/269; 260/112 R

[56] References Cited
UNITED STATES PATENTS 3,709,868  1/1973  Spector .............................. 424/1 X

OTHER PUBLICATIONS

Banerjee et al., Chemical Abstracts, vol. 71, No. 7, Aug. 18, 1969, Abstract No. 27443Z.

*Primary Examiner*—Benjamin R. Padgett
*Assistant Examiner*—Christine M. Nucker
*Attorney, Agent, or Firm*—Samuel L. Welt; George M. Gould

[57] ABSTRACT

The preparation of antigens and their selective antibodies for antipyrine therefrom as well as an immunoassay for antipyrine using said antibodies is described. Such radioimmunoassay can be utilized to determine an individual's antipyrine half-life which has been correlated with the genetically controlled level of benzo[a]pyrene hydroxylase induction. The latter measurement has been associated with risk to bronchogenic carcinoma. Thus determination of the antipyrine half-life by means of the instant radioimmunoassay can be used as a screening test for identifying individuals at special risk to lung cancer.

11 Claims, No Drawings

IMMUNOASSAY OF ANTIPYRINE

BACKGROUND OF THE INVENTION

Antipyrine (2,3-dimethyl-1-phenyl-3-pyrazolin-5-one) is a known antipyretic and analgesic. One of its present main uses is to evaluate the rate of drug metabolism in man since the plasma high life of antipyrine is determined by its rate of metabolism.

Recently, Kellermann et al. reported in the New England Journal of Medicine, Vol. 289, No. 18 (Nov. 1, 1973) at page 934 that benzo[a]pyrene hydroxylase inducibility can be associated with risk to bronchogenic carcinoma.

More recently it has been found that there is a direct relationship between the half-life of an individual's plasma antipyrine levels and that individual's genetically controlled level of benzo[a]pyrene hydroxylase induction as measured in isolated lymph-ocytes. See Kellerman et al., Drug Metabolism and Disposition (in press).

The present technique for determining antipyrine plasma levels is based on colorimetric procedures. Use of radioimmunoassay for this purpose would provide an improvement in sensitivity of several magnitudes. Thus it would be possible to obtain more accurate estimates of antipyrine half lives by allowing determinations for this compound over a significantly longer period of time after drug ingestion. In addition lower doses of antipyrine can be used for the test thus decreasing the possible risk of toxic side effects from the drug to the subjects.

DESCRIPTION OF THE INVENTION

The present invention relates to an immunoassay, particularly a radioimmunoassay for antipyrine employing novel antibodies which are selective for this compound and to novel antigens useful in eliciting the aforesaid antibodies. Such radioimmunoassay is about 1,000-fold more sensitive than the presently employed colorimetric technique for assaying for antipyrine and yet is still a relatively simple and rapid procedure.

The antigens employed in the present invention comprises antipyrine or derivatives thereof covalently bonded through a suitable linking group to a conventional immunogenic carrier material. As used herein the term "immunogenic carrier material" is meant to include those materials which have the property of independently eliciting an immunogenic response in a host animal and which can be covalently coupled to the antipyrine hapten. Suitable carrier materials include for example, proteins; natural or synthetic polymeric compounds such as polypeptides, e.g., polylysine or copolymers of amino acids; polysaccharides; and the like. Particularly preferred carrier materials are proteins and polypeptides, especially proteins.

The identity of the protein material utilized in the preparation of an antigen of the instant invention is not critical. Examples of suitable proteins useful in the practice of this invention include mammalian serum proteins such as, for example, human gamma globulin, human serum albumin, bovine serum albumin, methylated bovine serum albumin, rabbit serum albumin and bovine gamma globulin. Bovine serum albumin is a preferred protein material. Other suitable protein materials will be suggested to one skilled in the art. It is generally preferred but not critically necessary that protein materials be utilized which are foreign to the animal hosts in which the resulting antigen will be employed.

The covalent coupling of the antipyrine hapten to the immunogenic carrier material can be carried out in a number of ways employing procedures well known in the art.

One suitable procedure involves utilizing antipyrine per se by reacting that compound with the diazonium salt of an aromatic linking group such as the diazonium salt of p-aminobenzoic acid in a manner known per se. The aromatic linking group would then be bound through the diazo bond to the phenyl portion of the antipyrine molecule. The carboxylic acid group is then utilized to effect coupling to the immunogenic carrier material by means of coupling procedures hereinafter described.

Another process for preparing the subject antigen utilizes a derivative of antipyrine as the starting material. A preferred starting material is antipyrine substituted in the 4-position with a functional group that will react via amine, ester or amide bond formation with the desired linking group. Preferred functional groups for this purpose are the hydroxy and amino groups.

In one process variant the aforesaid 4-substituted antipyrine is reacted with the anhydride of a $C_4$ alkanoic dicarboxylic acid in an inert organic solvent medium such as a halogenated hydrocarbon, preferably methylene chloride at a temperature from about 4° to 20° C. A preferred alkanoic dicarboxylic acid for this purpose is succinic anhydride. The free carboxylic acid group in the reaction product is then used in the coupling reaction with the immunogenic carrier material as hereinafter described.

A further process variant involves reacting 4-amino antipyrine with an alkali salt of a halo $C_{1-7}$ lower alkanoic acid. Suitable halo lower alkanoic acids for this purpose include beta-halo acetic acid, γ-halopropionic acid, δ-halobutyric acid and the like.

The alkali salts useful in the practice of this process variant include the sodium, potassium and lithium salts; the sodium salt being of greatest preference. Halo derivatives of the aforesaid alkanoic acids include the chloro, bromo, iodo and fluoro derivatives. A preferred derivative for the purposes of this invention is sodium beta-chloroacetate. The reaction between 4-aminoantipyrine and the haloalkanoic acid is facilitated by conducting it in the presence of a suitable inert organic solvent such as a $C_{1-7}$ lower alkanol, e.g., ethanol. Most preferably the solvent system is anhydrous and thus an absolute lower alkanol is employed. The reaction is conveniently carried out at a temperature in the range between room temperature and 50°C.

Alternatively, the 4-aminoantipyrine may be reacted with a p-nitrobenzoyl halide, e.g., p-nitrobenzoyl chloride. The resulting nitro benzamide product may then be reduced with either hydrogen in the presence of a noble metal catalyst or chemically by use of a metal e.g., iron, tin, or zinc in acid solution in a manner know per se.

The resulting p-phenylamine compound can then be diazotized as before and coupled to the immunogenic carrier material.

In another process aspect, the phenyl group of antipyrine can be derivitized such as for example by nitration followed by reduction to yield the p-amino functional group. Diazotization in the usual manner followed by coupling with the immunogenic carrier material will yield the desired antigen. This procedure would be available when the immunogenic carrier material has aromatic sites available for coupling with a diazonium salt. Such salts are provided by aromatic amino acids such as phenylalanine or tyrosine for example.

Alternate pathways employing the derivatized phenyl group of antipyrine may also be utilized. Thus, for example, the p-amine group can be reacted with any of the aforesaid linking groups which in turn can be coupled to the immunogenic carrier material.

Another variant involves decomposing the diazonium salt of the p-amino derivative to the corresponding phenol in a manner known per se. The phenol derivative can then be reacted with a $C_{1-}$ alkanoic dicarboxylic acid anhydride as before to provide a suitable compound for coupling to the immunogenic carrier material.

A preferred procedure in accordance with the present invention utilizes 4-aminoantipyrine which is reacted with succinic anhydride to produce the desired hapten.

The covalent coupling of a hapten to the immunogenic carrier material can be carried out in a manner well known in the art for establishing amide or ester bonds. In some cases where it is desirable to ensure an adequate degree of coupling under the mildest conditions to minimize any possible deleterious effect on the carrier material it may be desirable to convert such hapten to an isolatable activated form prior to coupling. A suitable isolatable activated form is the N-hydroxysuccinimide ester of the carboxyl moiety in the linking group. Other suitable isolatable activated derivatives include the p-nitrophenyl esters; acylimidazoles; and the like.

Methods which do not require the isolation of activated intermediates may also be employed such as by utilizing EEDQ (N-ethoxycarbonyl-2-ethoxy-1,2-dihydroquinoline) as coupling agent or most preferably by using the mixed anhydride method.

The mixed anhydride method involves activating a carboxyl group of the hapten without isolation of an intermediate and then adding the activated hapten to the immunogenic carrier material. An example of such a reaction is the mixed anhydride obtained by reaction of the hapten with isobutylchloroformate. The hapten is dissolved in an anhydrous, water-miscible organic solvent such as dimethylformamide or dioxane and the solution is neutralized with an equimolar quantity of triethylamine. After stirring at room temperature the temperature of the mixture is reduced to between 0° and 8°C. A light (10%) molar excess of isobutylchloroformate is then added and stirring is continued. The immunogenic carrier material in water solution is then added to the chlorocarbonate derivative in solution and coupling is allowed to proceed for 30 minutes to overnight.

After dialysis in 50% dimethylformamide, 0.005 M tris buffer and distilled water, the conjugate is lyophilized and stored at reduced temperature (4°C.)

Alternate coupling procedures may also be employed. Thus, for example, in one such technique the immunogenic carrier material and a coupling agent are dissolved in a suitable inert solvent followed by addition of the desired hapten having a free carboxyl group. Reaction is carried out at a temperature in the range of from about 0° to about 50°C., preferably at about room temperature.

The coupling agent which may be used in the above reaction will be selected from those commonly employed in organic chemistry for initiating amide or ester bond formation. A suitable group of coupling agents comprise the carbodiimide or 1-ethyl-3-(3-dimethylaminopropyl) carbodiimide. The molar ratio of the hapten to the carrier material will, of course, depend on the identity of the hapten utilized and the carrier material selected for the reaction.

When utilizing carbodiimides as coupling agents it is desirable to utilize a slightly acidic reaction medium for this step, i.e., a medium having a pH in the range of from about 4 to 6.5, most preferably in the range of from about 4 to 6.5. Upon completion of the reaction the excess hapten molecules may be removed by dialysis.

In those process variants where an activated derivative of antipyrine is employed in isolatable form, it is desirable to prepare such compounds by reacting a carboxyl containing derivative of antipyrine with the desired activating compound such as N-hydroxysuccinimide, and a coupling agent, such as dicyclohexylcarbodiimide in an inert solvent. The reaction is usually allowed to proceed for 16–60 hours at reduced temperatures (0°–5°C.). The activated derivative may then be isolated by filtering off the by-product, dicyclohexylurea and concentrating off the solvent.

The resulting activated hapten may then be covalently bonded to the immunogenic carrier material by contacting the two components in solution. Thus, for example, when the activated hapten comprises the N-hydroxysuccinimide ester the immunogenic carrier material is bovine serum albumin, the activated derivative is dissolved in a water-miscible organic solvent and is added to an aqueous solution of the carrier material containing a base such as sodium bicarbonate.

Coupling of a diazonium salt form of the antipyrine hapten with the immunogenic carrier material can also be conveniently carried out using procedures well known in the art. Thus an aqueous solution of the diazonium salt can be added slowly to an aqueous solution of the carrier material at a temperature in the range of from about 0° to 4° C. until the reaction is completed, i.e., from 4 to 16 hours. The coupled product is isolated by dialysis and then lyophilized.

The antipyrine antigens hereinabove described may be utilized to induce formation of antibodies specific to antipyrine in host animals by injecting the antigen in such a host animal, preferably using an adjuvant. Improved titers can be obtained by repeated injections over a period of time. Suitable host animals for this purpose include mammals such as rabbits, horses, goats, guinea pigs, rats, cows, sheep, etc. The resulting antisera will contain antibodies which will selectively complex with antipyrine.

The antibodies of the present invention are useful as reagents for the determination of antipyrine concentration in biological fluids, preferably plasma. In one useful assay procedure, a known amount of labelled antipyrine is mixed with the above antibody and a sample containing antipyrine is added. The amount of antipyrine in the sample can be determined by measuring the inhibition of the binding to the antipyrine antibody of the labeled antipyrine by the sample and comparing the value observed with a standard curve previously developed. The reagents may be added in any order. A suitable assay procedure of this purpose is described in greater detail in U.S. Pat. No. 3,709,868.

Suitable labeled antipyrine for assay purposes include radioisotopically labeled antipyrine, particularly labeled with tritium ($^3$H), carbon 14($^{14}$C), or with iodine 125($^{125}$I). One may also employ antipyrine labeled with any other unique and detectable label such as for example an electron spin resonance group. Examples of the use of various electron spin resonance labeled molecules in bioassays are to be found in U.S. Pat. Nos. 3,453,288, 3,481,952 and 3,507,876. Other suitable labels include chromophores, fluorophors, enzymes, red blood cells, latex particles, etc.

The novel antigens and antibodies of the present invention may be utilized in conjunction with conventional additives, buffers, stabilizers, diluents, or in combination with other physiologically active substances. The preparation and use of compositions containing antigens or antibodies in conjunction with physiologically acceptable adjuvants is now well known in the art.

EXAMPLE 1

Preparation of Protein Conjugate

4-Aminoantipyrine (0.1 mmole) in 10 ml. methylene chloride was mixed with succinic anhydride (0.11 mmole) in 5 ml. methylene chloride and allowed to react at 20° for 1 hour. The resulting precipitate, after washing three times in methylene chloride, was distinct from the two starting compounds on silica gel thin layer chromatograms (methanol-chloroform - 10:90 solvent system). Mass spectral analysis was consistent with the formation of the expected 4-aminosuccinamide derivative of antipyrine (4-ASAP). 4-ASAP was reacted with isobutylchloroformate in the presence of triethylamine for 20 minutes at 4° in N,N-dimethylformamide. The resulting chlorocarbonate derivative was allowed to react directly with bovine serum albumin (BSA) to form a protein conjugate via the epsilon amino group of lysine. After dialysis in 50% DMF, 0.005 M Tris and finally distilled water, the conjugate was lyophilized and stored at 4°.

Characterization of the conjugate by fluorometric analysis with fluorescamine indicated that 18 moles of 4-ASAP had been covalently coupled to 1 mole of BSA.

EXAMPLE 2

Immunization Procedure

The 4-ASAP-BSA conjugate (2 mg.) was dissolved in 1 ml. PBS and emulsified in an equal volume of Freund's complete adjuvant (FCA) of Freund's incomplete adjuvant (FIA). The immunization schedule for antibody production in a New Zealand albino rabbit was as follows:

| Innoculation No. | Day | Amount Injected ($\mu$g) | Site |
|---|---|---|---|
| 1 | 1 | 500, FCA | i.d. (12 sites) |
| 2 | 23 | 10 | i.v. |
| 3 | 27 | 20 | i.v. |
| 4 | 37 | 500, FIA | i.d. |
| 5 | 78 | 100 + 100 | i.v. + i.d. |
| 6 | 114 | 100 | i.v. |
| 7 | 117 | 100 | i.v. |

EXAMPLE 3

Antibody Production

The bleeding schedule and antibody titers were as follows:

| Bleeding No. | Day | Serum Dilution | % H$^3$ AP bound |
|---|---|---|---|
| 1 | 21 | 1:10 | 24 |
| 2 | 30 | 1:20 | 45 |
| 3 | 62 | 1:30 | 60 |
| 4 | 90 | 1:50 | 63 |
| 5 | 119 | | |

Using serum obtained on day 90 or 119 and diluted 1:70, the concentration of antipyrine (AP) which caused a 50% inhibition of the antibody-H$^3$AP complex was 10 ng. A concentration of 50 ng AP/ml plasma can be readily assayed using 20 $\mu$l of plasma. A five-fold further increase in sensitivity can be obtained by using 100 $\mu$l of plasma. 4-Aminoantipyrine inhibits complex formation by 50% at a slightly higher concentration than AP.

EXAMPLE 4

Method of Radioimmunoassay of Antipyrine

The following stock reagents and materials were used:

1. The assay tubes were 12 × 75 mm disposable culture tubes.
2. A solution of antipyrine-N-methyl-$^3$H (specific activity 170 $\mu$Ci/$\mu$mole; New England Nuclear) in phosphate buffered saline (PBS) pH 7.2 to give 50,000 cpm/ml.
3. Antiserum diluted 1:50 with PBS containing 0.1% sodium azide.
4. Standard solutions of unlabelled antipyrine in PBS: 10, 50, 200, and 1000 ng/ml.

A volume of 0.1 ml. of control human plasma diluted with four volumes PBS was added to 0.1 ml. of each standard of antipyrine in order to generate a calibration curve of 1 to 100 ng/tube. The same volume of the diluted unknown plasma samples prepared from heparinized blood was added to tubes containing 0.1 ml. of PBS. Two blanks were included by adding the control plasma to 0.1 ml. PBS. The 0.1 ml. (5,000 cpm) of the antipyrine-N-methyl-$^3$H solution was added to each tube followed by 0.1 ml. of the antiserum solution to all tubes except one of the blanks. The volume in each tube was brought to 1 ml. with PBS. After mixing on a vortex, the tubes were kept at room temperature for 30 minutes and then stored at 4° for 2 hours.

An equal volume (1 ml.) of saturated ammonium sulfate was then added to precipitate globulin-bound antipyrine. After thorough mixing on a vortex and allowing to stand at 4° for 15 minutes, the tubes were centrifuged at 3,000 rpm for 30 minutes at 4°. The supernatant containing unbound antipyrine-N-methyl-$^3$H was decanted into a counting vial and 10 ml. of scintillator added. The vial was then vortexed for 10 seconds to extract the radioactive material into the organic phase, and each sample was counted.

Unknown saliva samples are assayed for antipyrine in a completely analogous procedure, except that assay tubes received 20 $\mu$l of control human plasma to provide sufficient protein for ammonium sulfate precipitation of the antibody-antipyrine complex. Saliva samples were centrifuged for 20 minutes at 1500 × g prior to assay, and the resulting supernatant was used for the determinations. The procedure readily detects 1 to 100 ng antipyrine per tube giving a limit of sensitivity of 50 ng antipyrine/ml plasma of saliva using a 20$\mu$l sample.

We claim:

1. An antigen consisting essentially of antipyrine or a derivative thereof covalently bonded to an immunogenic carrier material through a linking group, wherein said antipyrine derivative is antipyrine substituted in the 4-position with a functional group that will react via amine-ester or amide bond formation with the said linking group.

2. The antigen of claim 1 wherein said immunogenic carrier material is bovine serum albumin.

3. The antigen of claim 1 wherein said derivative of antipyrine is 4-aminoantipyrine.

4. The antigen of claim 1 wherein said linking group is a succinate radical.

5. The antigen of claim 1 which is 4-aminoantipyrine covalently bonded to bovine serum albumin through a succinate linking group.

6. An antibody specific to antipyrine prepared by innoculating a host animal with the antigen of claim 1 and collecting the serum from said host animal.

7. The antibody of claim 6 wherein said antigen consists essentially of 4-amino antipyrine covalently bonded to bovine serum albumin through a succinate linking group.

8. A method for the assay of antipyrine in a sample, which method comprises mixing said sample with a known amount of a labelled antipyrine compound and an antibody to the antigen of claim 1 which will selectively complex with said antipyrine compound, said antibody being elicited by use of an antigen of claim 1, measuring the degree of binding of the said labelled antipyrine compound, and determining the amount of antipyrine present in said sample by comparing said degree of binding to a standard curve obtained by mixing known amounts of said antipyrine compound with fixed amounts of said labelled antipyrine compound and said antibody and determining the degree of binding for each known amount of said antipyrine compound.

9. The method of claim 8 wherein radiolabelled antipyrine compound is used.

10. The method of claim 9 wherein said radiolabelled antipyrine compound is antipyrine-N-methyl-$^3$H.

11. 4-amino succinamide antipyrine.

* * * * *